(12) United States Patent
Muller et al.

(10) Patent No.: US 8,920,028 B2
(45) Date of Patent: Dec. 30, 2014

(54) TEST PHANTOM FOR TOMOGRAPHIC IMAGING AND NOTABLY FOR BREAST TOMOSYNTHESIS

(75) Inventors: Serge Muller, Guyancourt (FR); Laurence Vancamberg, Le Port-Marly (FR); Razvan Iordache, Paris (FR); Remy Klausz, Neuilly sur Seine (FR)

(73) Assignee: General Electric Company, Schenectady, NY (US)

( * ) Notice: Subject to any disclaimer, the term of this patent is extended or adjusted under 35 U.S.C. 154(b) by 312 days.

(21) Appl. No.: 13/370,698

(22) Filed: Feb. 10, 2012

(65) Prior Publication Data

US 2012/0207283 A1 Aug. 16, 2012

(51) Int. Cl.
*G01D 18/00* (2006.01)
*A61B 6/00* (2006.01)
*A61B 5/00* (2006.01)
*A61B 6/02* (2006.01)

(52) U.S. Cl.
CPC .......... *A61B 6/502* (2013.01); *A61B 6/583* (2013.01); *A61B 6/025* (2013.01); *A61B 5/4872* (2013.01)
USPC ...................................................... 378/207

(58) Field of Classification Search
CPC .......... A61B 6/032; A61B 6/583; A61B 6/03; A61B 6/4035; A61B 6/482; A61B 6/502; G06T 7/0012; G06T 2207/10116
USPC ............................................ 378/18,204, 207
See application file for complete search history.

(56) References Cited

U.S. PATENT DOCUMENTS 4,655,716 A 4/1987 Hoevel
7,289,654 B2 10/2007 Muller

FOREIGN PATENT DOCUMENTS

FR 2857484 A 1/2005
WO 2008021720 A2 2/2002

OTHER PUBLICATIONS

Vollmar et al., ("Breast Phantom Design for Dedicated Breast CT and Breast Tomosynthesis." WC 2009, IFMBE Proceedings 25/II, pp. 53-56, 2009).*
Search Report and Written Opinion for corresponding French Application No. 1151148, dated Sep. 27, 2011.
Kimme-Smith Carolyn et al., "A Review of Mammography Test Objects for the Calibraton of Resolution, Contrast, and Exposure", Medical Physics, vol. 16, No. 5, Sep. 1, 1989, pp. 758-765.
Pachoud, Marc et al., A new test phantom with different breast tissue compositions for image quality assessment in conventional and digital mammography, Physics in Medicine and Biology, vol. 49, No. 23, Dec. 7, 2004, pp. 5267-5281.
Vollmar, S.V. et al., "Breast Phantom Design for Dedicated Breast CT and Breast Tomosynthesis", IFMBE Proceedings, 25/II, 2009, pp. 53-56.

* cited by examiner

*Primary Examiner* — Courtney Thomas
(74) *Attorney, Agent, or Firm* — GE Global Patent Operation; Marc A. Vivenzio

(57) ABSTRACT

A test phantom for tomographic imaging, the phantom comprising an assembly of elementary structures defining a 3D mesh, wherein each elementary structure comprises a chief constituent material corresponding to an X-ray attenuation simulating a glandularity, wherein the elementary structures are in at least two types of chief constituent materials corresponding to different X-ray attenuations.

10 Claims, 3 Drawing Sheets

TEST PHANTOM FOR TOMOGRAPHIC IMAGING AND NOTABLY FOR BREAST TOMOSYNTHESIS

BACKGROUND OF THE INVENTION

1. Field of the Invention

Embodiments of the present invention relate to a test phantom for tomographic imaging. More particularly, embodiments of the present invention may be applied to breast tomosynthesis.

2. Description of the Prior Art

For many years it has been known, especially in mammography, to use test phantoms for testing performance levels of equipment. In one particular example, these test objects are in the form of a supporting structure on which a test slab in wax is placed, small structures are embedded in the test objects to model, for example, micro-calcifications, fibrous structures or tumours.

These test phantoms, for example those marketed by CIRS (CIRS 015) or Gammex (Gammex 156), are given particular use under the ACR accreditation program ("American College of Radiology").

Test phantoms are also known to be used in mammography to calibrate or evaluate artefacts, and are in the form of fully homogeneous slabs.

More recently, phantoms for breast mammography have also been proposed in which each phantom has a substrate in a material, in radiological terms, that is equivalent to the adipose envelope of the breast, this substrate being conformed to imitate the shape of the breast. Two types of substrates are provided, ring phantoms either in the shape of a compressed breast or in the form of a pendant breast.

At the center of each substrate is a cubic housing intended to receive assemblies of elementary structures of slab or cube type. Inserts intended to reproduce micro-calcifications or fibres are embedded in these elementary structures. Provision is also made so that elementary cubes devoid of any insert can be used to test the observer.

It is also desirable, notably in mammography, to be able to detect not only micro-calcifications, fibrous structures or tumours, but also to be able to evaluate the glandularity of tissues, i.e. the percentage of fibroglandular tissue contained in total fibroglandular and adipose tissue.

Methods for the digital processing of images have been proposed in this respect, but are not yet fully satisfactory. In particular, the methods only allow binary classification between dense tissue and fatty tissue, but fail to give full satisfaction.

For tomography or tomosynthesis, there is also a need for tools that can be used to assess, notably quantitatively, the rendering of images produced by the tomographic or tomosynthesis device. For mammography, in particular, the low number of acquired projections and limited angle views can lead to bias with respect to voxel values which, for practitioners, does not contribute to facilitating evaluation of the glandularity of mammary tissue in available images.

BRIEF SUMMARY OF THE INVENTION

In accordance with an embodiment of the present invention, there is provided a test phantom for tomographic imaging, the phantom comprises an assembly of elementary structures defining a 3D mesh, wherein each elementary structure comprises a chief constituent material corresponding to an X-ray attenuation simulating a glandularity, wherein the elementary structures are in at least two types of chief constituent materials corresponding to different X-ray attenuations.

In accordance with another embodiment of the present invention, there is provided an assembly of elementary structures, the assembly defines a 3D mesh for a test phantom in tomographic imaging, wherein each elementary structure comprises a chief constituent material corresponding to an X-ray attenuation simulating a glandularity, wherein the elementary structures are in at least two types of chief constituent materials corresponding to different X-ray attenuations.

In accordance with another embodiment of the present invention, there is provided a method for tomographic imaging, the method comprises acquiring tomography or tomosynthesis images of a test phantom, the phantom comprising an assembly of elementary structures defining a 3D mesh, wherein each elementary structure comprises a chief constituent material corresponding to an X-ray attenuation simulating a glandularity, wherein the elementary structures are in at least two types of chief constituent materials corresponding to different X-ray attenuations; comparing the images acquired with a mapping of the assembly of elementary structures of the test phantom; and processing detected errors to infer information on the quality of an imaging device or of processing for 3D reconstruction.

BRIEF DESCRIPTION OF THE DRAWINGS

Characteristics and advantages of different embodiments of the present invention will become apparent from the following description, which is purely illustrative and non-limiting, and is to be read in connection with the appended figures in which.

DETAILED DESCRIPTION OF THE INVENTION

Figure 1:
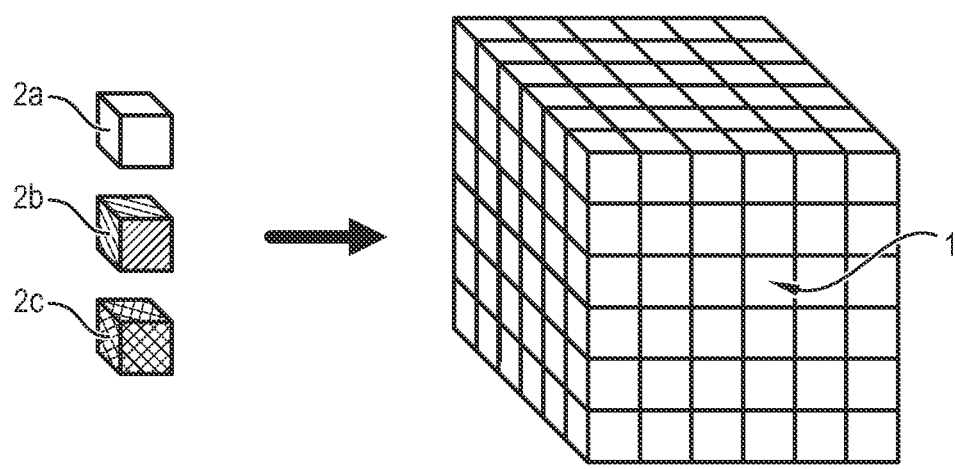
FIGS. 1 and 2 are schematic illustrations of an assembly of elementary cubes defining a test phantom according to an embodiment of the invention.
Figure 2:
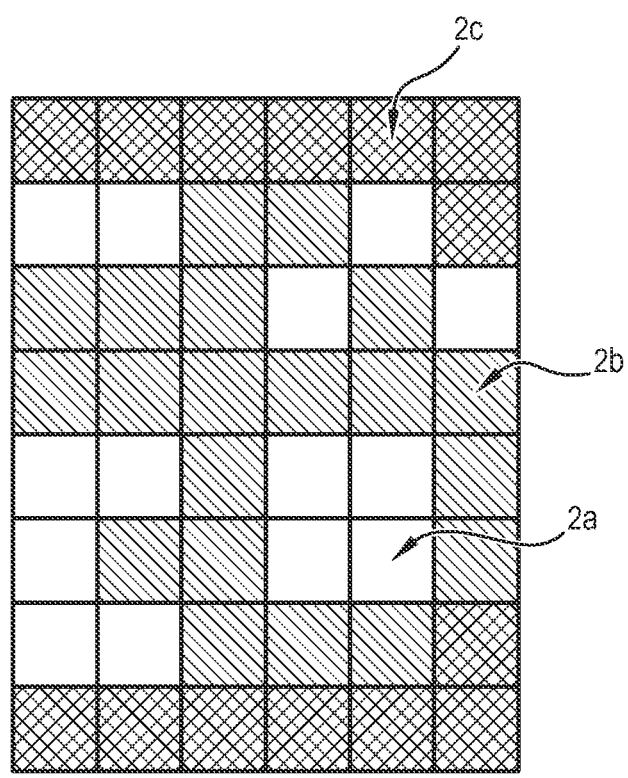

A test phantom 1 is illustrated in FIG. 1. In one embodiment, the test phantom 1 is a 3D structure, parallelepiped, and formed from elementary structures 2a, 2b, 2c. As used herein, the term "elementary structures" is intended to be representative of any elements which can be assembled to form a 3D meshing of a volume.

In the embodiment illustrated in FIG. 1, the elementary structures 2a, 2b, 2c are elementary cubes which are assembled one on another to form the parallelepiped 1.

These elementary cubes 2a, 2b, 2c can be of several different types, wherein each type corresponds to a different chief constituent material. Test phantoms made from elementary structures corresponding to only two types of constituent material can be envisaged. Test phantoms made from elementary structures corresponding to three or more types of constituent materials are also possible.

These different types of constituent materials correspond to different X-ray attenuations and simulate different glandularities.

In one embodiment, test phantoms are made from three different types of elementary cubes 2a, 2b, 2c corresponding to three types of constituent materials, wherein elementary cubes 2a correspond to attenuation simulating a glandularity of 100% (such as allowed by BR 100/0 (CIRS) for example), elementary cubes 2b correspond to attenuation simulating a glandularity of 50% (BR50/50 (CIRS)), and elementary cubes 2c corresponds to attenuation simulating a glandularity of 0% (cubes in BR 0/100 (CIRS)), or possibly high density polyethylene)

Materials other than the specific materials given here by way of example may evidently be envisaged.

In one embodiment, the elementary structures 2a, 2b, 2c are each homogeneous and do not integrate an insert.

The elementary structures measure 1×1×1 cm$^3$ and are assembled to form a parallelepiped 1 whose size is comparable to the height of a compressed breast in one direction (2-8 cm) and whose sides are comparable to the dimension of the compressed breast arranged on the platforms of mammography equipment, i.e. at least 5 cm×5 cm and no more than 20 cm×30 cm.

With these dimensions, the parallelepiped 1 (assembly of elementary structures) may, alone, form the test phantom to be imaged. In mammography, for example, the test phantom may simulate the meshwork of a whole breast independently without a container in which the assembly could be placed.

The elementary structures may all be of the same size or of different sizes, while the elementary structures of the same order of magnitude for example. It is possible, in one embodiment for example, to assemble cubes of 1×1×1 cm with cubes of 0.5×0.5×0.5 cm. It is therefore possible to replace 1 cube of 1×1×1 cm by 8 cubes of 0.5×0.5×0.5 cm having different compositions to obtain more local details on glandularity. This embodiment has the advantage of faster reconstruction of homogeneous regions or volume using cubes of larger size. Elementary slabs or elementary bars can also be envisaged instead of cubes.

Shapes other than cubic structures can evidently be envisaged for the elementary structures, notably any polyhedron structure and preferably those allowing compact pixelization.

Beveled cubic structures can also be envisaged for some elementary structures, for example, to impart shapes other than right angles to the contour of the assembly.

The elementary structures thus formed are assembled together to form the structure of the desired phantom, which itself may be of different shapes and is not limited to parallelepipeds.

Using glue for assembly is possible. In some embodiments, if it is desired to use the same elementary structures in different arrangements, repositioning glue may be used. Provision may also be made so that the elementary structures are of an elementary shape allowing them to be press-fitted into each other.

Additionally, the assembly thus formed may optionally be immersed in a material such as water or gel if the contact between the faces of the elementary structures is not perfect, so as to avoid interstices between the faces of the elementary structures which do not absorb X-rays. If a liquid is used, a container structure may be provided wherein the container does not have any radiological effect. It is also possible to form the assembly at a temperature at which the interstice filling fluid is liquid, then cool the assembly to a temperature at which it becomes sufficiently viscous or solid to ensure the cohesion of all or part of the assembly at the same time. In one embodiment, it is possible to form the assembly in a type of mould, and to release it when the desired temperature has been reached.

Figure 3:
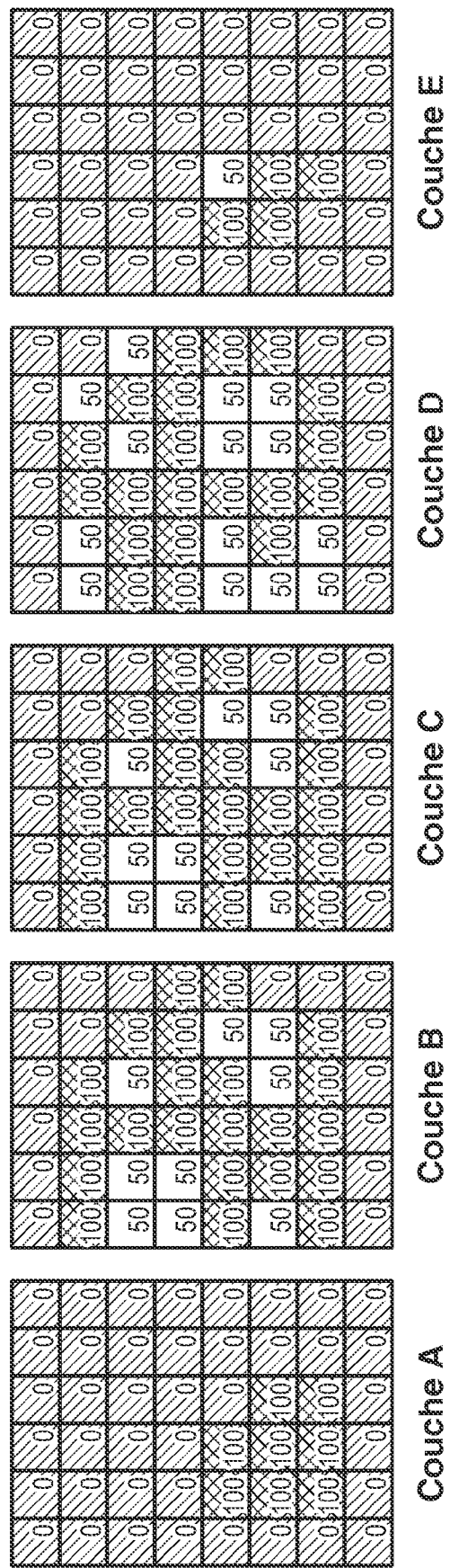
FIG. 3 illustrates an exemplary mapping of different layers forming a test phantom.

FIG. 3 illustrates a 6×8×5 parallelepiped assembly comprising elementary cubes 2a, 2b, 2c. This assembly is formed layer by layer (five layers referenced A to E) in relation to the mapping it is desired to test.

In one embodiment, assembling is made using sets of elementary structures 2a, 2b, 2c, e.g. sachets containing structures of different types, and optionally mappings to be produced. It is pointed out here that the elementary cubes or structures may be of different colors to facilitate handling thereof and mapping set-up.

The test phantoms just described also allow the testing of devices used for imaging or of processing for 3D image reconstruction.

Test phantoms described herein allow for the evaluation, possibly the quantitative evaluation, of the reliability of a tomography or tomosynthesis imaging device in terms of the rendering of glandularity.

Figure 4:
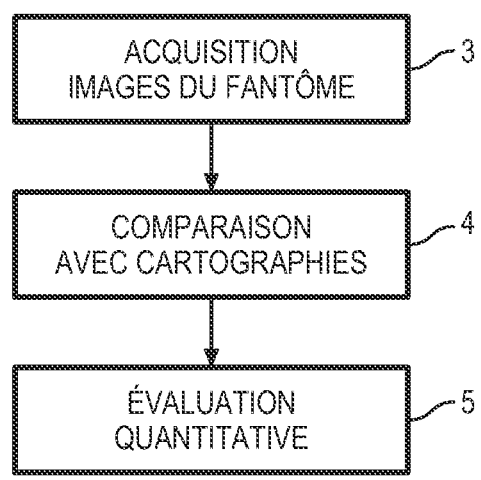
FIG. 4 illustrates different steps performed to test an imaging device or to test processing for reconstructing the 3D image, using a test phantom of the type shown in FIGS. 1 to 3.

As illustrated in FIG. 4, after positioning a given phantom on the imaging device, images of this phantom are acquired 3 and the slices obtained are compared 4 with the slices obtained with phantom mapping of the same slice to detect any errors in the meshing of the elementary structures.

Any detected errors are processed for quantitative evaluation 5 of the imaging device or, in tomosynthesis, for quantitative evaluation of the 3D reconstruction algorithm used.

Processing can be particularly simple and consist of recording the number or percentage of errors from given test phantoms.

To increase the efficiency of the test, it is possible to conduct the test successively on different configurations of the phantom obtained by re-arranging the elementary structures at the end of each test, thereby forming the equivalent of a new phantom with various proportions and distributions of the different types of elementary structures.

What is claimed is:

1. A test phantom for tomographic imaging, the phantom comprising an assembly of elementary structures defining a 3D mesh, wherein each elementary structure comprises a chief constituent material corresponding to an X-ray attenuation simulating a glandularity, wherein the elementary structures are in at least two types of chief constituent materials corresponding to different X-ray attenuations; the test phantom being substantially formed by the assembly of the elementary structures, wherein the test phantom forms a simulation of an object to be imaged by tomographic imaging.

2. The test phantom according to claim 1, wherein each of the elementary structures are individual homogeneous structure.

3. The test phantom according to claim 1, wherein the elementary structures are in at least three types of chief constituent materials corresponding to different X-ray attenuations.

4. The test phantom according to claim 3, wherein the elementary structures comprise three types of chief constituent materials corresponding to attenuation simulating 100% glandularity, attenuation simulating 50% glandularity and attenuation simulating 0% glandularity.

5. The test phantom according to claim 1, wherein the elementary structures are polyhedrons.

6. The test phantom according to claim 5, wherein the elementary structures are polyhedrons of different sizes, wherein the assembly of elementary structures of smaller size is substituted for an elementary structure of larger size.

7. The test phantom according to claim 5, wherein the assembly comprises at least one side having a dimension equal to or more than 5 cm.

8. The test phantom according to claim 1, wherein the assembly is immersed in water or gel or comprises a filler material to ensure the cohesion of all or part of the assembly at the same time.

9. An assembly of elementary structures, the assembly defining a 3D mesh for a test phantom in tomographic imaging, wherein each elementary structure comprises a chief constituent material corresponding to an X-ray attenuation simulating a glandularity, wherein the elementary structures comprise at least three types of chief constituent materials corresponding to different X-ray attenuations, including attenuation simulating 100% glandularity, attenuation simulating 50% glandularity and attenuation simulating 0% glandularity.

10. A method for tomographic imaging, the method comprising:
- acquiring tomography or tomosynthesis images of a test phantom, the test phantom comprising an assembly of elementary structures defining a 3D mesh, wherein each elementary structure comprises a chief constituent material corresponding to an X-ray attenuation simulating a glandularity, wherein the elementary structures are in at least two types of chief constituent materials corresponding to different X-ray attenuations; the test phantom being substantially formed by the assembly of the elementary structures;
- comparing the images acquired with a mapping of the assembly of elementary structures of the test phantom; and
- processing detected errors to infer information on the quality of an imaging device or of processing for 3D reconstruction.

* * * * *